(12) United States Patent
Paek et al.

(10) Patent No.: US 12,076,565 B2
(45) Date of Patent: Sep. 3, 2024

(54) IMPLANTABLE MEDICAL DEVICE CONTROL SYSTEM AND CONTROL METHOD THEREFOR

(71) Applicant: SNU R&DB FOUNDATION, Seoul (KR)

(72) Inventors: Sun Ha Paek, Seoul (KR); Yong Hoon Lim, Seoul (KR); Hyung Woo Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 890 days.

(21) Appl. No.: 17/059,367

(22) PCT Filed: May 31, 2019

(86) PCT No.: PCT/KR2019/006585
§ 371 (c)(1),
(2) Date: Nov. 27, 2020

(87) PCT Pub. No.: WO2019/231282
PCT Pub. Date: Dec. 5, 2019

(65) Prior Publication Data
US 2021/0187301 A1  Jun. 24, 2021

(30) Foreign Application Priority Data

May 31, 2018 (KR) .................. 10-2018-0063016
May 31, 2018 (KR) .................. 10-2018-0063017
May 31, 2018 (KR) .................. 10-2018-0063018

(51) Int. Cl.
*A61N 1/36* (2006.01)
*A61N 1/05* (2006.01)
(Continued)

(52) U.S. Cl.
CPC .......... *A61N 1/36139* (2013.01); *A61N 1/05* (2013.01); *A61N 1/375* (2013.01); *A61N 1/3787* (2013.01);
(Continued)

(58) Field of Classification Search
CPC ............ A61N 1/37282; A61N 1/36235; A61N 1/36139
See application file for complete search history.

(56) References Cited

U.S. PATENT DOCUMENTS

2005/0075542 A1* 4/2005 Goldreich .............. G16H 40/67
600/300
2011/0106213 A1* 5/2011 Davis ...................... G16Z 99/00
607/59

FOREIGN PATENT DOCUMENTS

KR      10-0877228 B1    1/2009
KR   10-2012-0011156 A   2/2012
(Continued)

*Primary Examiner* — Alyssa M Alter
(74) *Attorney, Agent, or Firm* — NKL LAW; Jae Youn Kim (57) ABSTRACT

Provided are an implantable medical device control system and a control method therefor, the system comprising: an implantable medical device implanted into the body so as to stimulate a specific area in the body; a management terminal for controlling the driving of the implantable medical device by communicating with the implantable medical device through a wireless communication method; and a management server connected with the management terminal so as to be capable of communicating therewith, assigning priority to each parameter included in patient condition information and storing and managing same, and providing the stored information, and thus, since priority is assigned to each parameter included in patient condition information and stimulation applied to a specific part in the body is adjusted according to the assigned priority, the entire param- (Continued)

eter can be controlled such that a patient condition is maintained in a stabilized state by satisfying a preset reference value.

3 Claims, 5 Drawing Sheets

(51) Int. Cl.
*A61N 1/375* (2006.01)
*A61N 1/378* (2006.01)
*G16H 20/30* (2018.01)
*G16H 40/60* (2018.01)
*G16H 50/30* (2018.01)

(52) U.S. Cl.
CPC ............ *G16H 20/30* (2018.01); *G16H 40/60* (2018.01); *G16H 50/30* (2018.01)

(56) References Cited

FOREIGN PATENT DOCUMENTS

| | | | |
|---|---|---|---|
| KR | 10-2012-0097985 A | 9/2012 |
| KR | 10-2012-0120818 A | 11/2012 |
| KR | 10-1371705 A | 3/2014 |
| KR | 10-2014-0049795 A | 4/2014 |
| KR | 10-2015-0042450 A | 4/2015 |
| KR | 10-2015-0138518 A | 12/2015 |
| KR | 10-2016-0099174 A | 8/2016 |
| KR | 10-1662594 B1 | 10/2016 |
| KR | 10-2017-0046593 A | 5/2017 |
| KR | 10-2017-0128017 A | 11/2017 |
| KR | 10-1929677 B1 | 12/2018 |

* cited by examiner

IMPLANTABLE MEDICAL DEVICE CONTROL SYSTEM AND CONTROL METHOD THEREFOR

BACKGROUND OF THE INVENTION

1. Field of the Invention

The present invention relates to an implantable medical device, and more particularly, to an implantable medical device control system that is implanted into the body to stimulate a specific part in the body and a method of controlling the same.

2. Description of the Related Art

In recent years, there have been developed an artificial organ for alleviating or treating symptoms of various diseases such as a pacemaker or the like, or various implantable medical devices such as cochlear implants, gastric stimulators, spinal cord stimulators, cardiac defibrillators, pacemakers, insulin pumps, foot drop implants, deep brain stimulation (DBS), and the like Among them, the deep brain stimulation device is an implantable medical device that relieves symptoms of brain disease by applying electrical stimulation to a specific part of the brain or nerves.

A deep brain stimulation device according to the related art includes an electrode implanted in the brain, a control device implanted in the chest to generate an electrical stimulation signal, and a connection line for connecting the electrode and the control device.

The control device includes a complex electronic circuit based on a microprocessor, a battery for driving for about 5 years, an RF transceiver for communication with an outside, etc., and uses the basic structure of a cardiac pacemaker itself which is contained in a titanium case specially manufactured for stable operation for a long period in a living body and sealed by laser welding.

Therefore, in the case of the deep brain stimulation device according to the related art, the manufacturing cost of the control device is expensive and the size of the control device is increased, so that the implantation area reaches the chest. Specifically, when the battery reaches the end of its life within 5 years, the control device has to be replaced with a new control device through surgery.

In order to solve the problems, there has been disclosed a deep brain stimulation device technology to which a wireless power transmission technology is applied in following patent document 1 and patent document 2.

In patent document 1, there has been disclosed a deep brain stimulation device where a rotating magnetic field is formed by a rotating magnetic field disk provided inside a hat worn by a patient, and induced power is generated by an induction coil plate fixed to the lower part of the patient's scalp to be combined with the formed rotating magnetic field, thereby driving the electrode implanted in the patient brain. Thus, it is possible to correct the abnormal movement and sensing function by using power supplied wirelessly from an outside of the body.

In patent document 2, there has been disclosed a ultra-compact deep brain stimulation system which includes an internal device implanted on the scalp, an external device for supplying power to the internal device in a wireless power transmission scheme, where a wireless power transmitter of the external device includes an external coil in which a magnetic field is induced by power supplied from a battery and an external magnet wound around the external coil, and a wireless power receiver of the internal device includes an inner coil that is aligned with the outer coil so that AC power is formed by a magnetic field induced in the outer coil, and, an inner magnet wound by an inner coil. Since the external magnet is attached to the internal magnet, the external coil and the internal coil are aligned and the external device is combined with the internal device, thereby combining the wireless power transmission function and eliminating the need for reoperation due to battery consumption.

Document of Related Art

Patent Document (Patent document 1) Korean Registered Patent No. 10-0877228 (published on Dec. 26, 2008)
(Patent document 2) Korean Registered Patent No. 10-1662594 (Published on Oct. 6, 2016)

SUMMARY OF THE INVENTION

A deep brain stimulation device to which the wireless power transmission technology according to the related art including patent documents 1 and 2 is applied generates induction power in a magnetic induction scheme between the rotating magnetic field disk and the induction coil plate provided in the external device and the internal device, and transmits the power to the internal device.

As a technology for wirelessly transmitting power into the human body, various schemes have been attempted to date, and largely, there are an electromagnetic induction scheme using electromagnetic waves, an electromagnetic resonance scheme, an electromagnetic wave scheme, an RF scheme using a radio frequency, and an ultrasonic scheme using ultrasonic waves.

The power transmission device using electromagnetic induction includes a charging module that generates charging power using an external power source, and a power receiving module that receives charging power through an electromagnetic induction phenomenon from the charging module. The technology is the closest technology to commercialization due to high efficiency.

However, as the transfer energy of electromagnetic waves rapidly decrease in inverse proportion to the square of the distance in the air, the power transmission device using electromagnetic induction is limited to the use of the charging module and the power receiving module within a few centimeters from each other.

For this reason, in the deep brain stimulation device to which the wireless power transmission technology using the electromagnetic induction scheme according to the related art, regardless of the load fluctuations in the internal device, as the external device continuously transmits power, the power of the battery provided in the external device is consumed, so that the power efficiency is reduced.

In addition, when a power receiver of an electromagnetic wave type embedded in the human body is applied, the power receiver acts as an antenna for a specific frequency band, and malfunctions due to electromagnetic interface (EMI) interference occur when external electromagnetic wave noise using the frequency of the corresponding band is present.

In addition, in the electromagnetic wave scheme, when the transmitter generates electromagnetic waves, the receiver receives the electromagnetic waves by using a plurality of rectennas in which an antenna and a rectifier are combined with each other and converts them into power, so that power can be transmitted over a long distance, but the yield is low and the electromagnetic wave itself is harmful to the human body.

In addition, the power transmission device using the radio frequency collects energy of RF having a very long propagation distance, and supplies power to an electronic device or a sensor. RF exists in the air, and its propagation distance is very wide. However, RF has a low energy density itself or a low energy amount after energy conversion is low.

The ultrasonic wireless power transmission scheme uses a piezoelectric effect of a ferroelectric material.

That is, when a compressive force or tensile force, which is a mechanical external force, is applied to both ends of a piezoelectric body, electricity is generated, and on the contrary, when an electric field is applied, the displacement of contraction or relaxation is generated. When the latter is used, ultrasonic waves may be generated, and when the former is used, electricity may be generated by the generated ultrasonic pressure.

Therefore, the ultrasonic wireless power transmission scheme uses such piezoelectric phenomenon to generate ultrasonic waves from the outside and transmit them to the inside of the human body, and then an ultrasonic receiver including an internal piezoelectric body converts acoustic energy (ultrasonic waves) into electrical energy to transmit power. Since ultrasonic waves are sound waves, unlike light, a medium is required to propagate, and the transmission speed varies depending on the characteristics of the medium layer.

Since 70% of human tissue is water, the transmission rate of ultrasonic waves in the body has a value similar to that in water.

For this reason, ultrasonic waves have been proven to be safe in the medical field and have been applied to patient diagnosis and medical devices.

When acoustic vibration generated from an ultrasonic device vibrates the transmission matching layer with the medium, and piezoelectric mechanical energy is transmitted to the receiving device through the matching layer that receives vibration, such ultrasonic waves may be used as wireless power.

A power transmission device using ultrasonic waves having the above characteristics includes a transmitting device that generates ultrasonic waves and a receiving device that receives the generated ultrasonic waves.

The power transmission device using ultrasonic waves may be used in various media such as underwater or human skin. However, when the transmitting device and the receiving device are separated from each other by a medium such as water or human skin, power transmission efficiency between the ultrasonic transmitting and receiving devices is reduced.

Therefore, there is a demand for the development of a technology capable of wirelessly supplying power to an internal device using ultrasonic waves and preventing a decrease in power transmission efficiency.

Meanwhile, a deep brain stimulation device according to the related art is manufactured to stimulate the brain and nerves according to a program preset by a doctor or manufacturer.

Therefore, the deep brain stimulation device according to the related art has limitations in appropriately treating according to various symptoms and progression levels for each patient, depending on the experience of a doctor or manufacturer.

For this reason, there is a demand for the development of a technology that can alleviate the symptoms caused by the disease and maximize the treatment effect by appropriately adjusting the drugs and the intensity of stimulation according to the actual symptoms or progression of a patient having a disease.

To solve the problems described above, an object of the present invention is to provide an implantable medical device control system capable of wirelessly transmitting power to an internal device implanted in the body using ultrasound outside the body, and a method of controlling the same.

Another object of the present invention is to provide an implantable medical device control system which is capable of assigning priority to various parameters for determining symptoms and progression of a patient with a disease, and adjusting the dose and administration cycle of a drug, and stimulation applied to a specific part of the body To provide a system according to the assigned priority, and a method of controlling the same.

Still another object of the present invention is to provide an implantable medical device control system which is capable of alleviating the symptoms of diseases and maximizing the treatment effect by controlling the intensity and cycle of stimulating a specific part of the body based on drug dose information, and a method of controlling the same.

Still another object of the present invention is to provide an implantable medical device control system which is capable of analyzing various parameters for determining symptoms and progression of a patient with a disease, and adjusting stimulation applied to a specific part of the body by reflecting the analysis result in real time, and a method of controlling the same.

Still another object of the present invention is to provide an implantable medical device control system which is capable of improving the therapeutic effect by adjusting stimulation applied to a specific part of the body in connection with information of another patient with the same disease as the patient, and a method of controlling the same.

Still another object of the present invention is to provide an implantable medical device control system which is capable of controlling the driving of a medical device by using internal information collected using medical devices implanted in the body and external information collected outside the body, and a method of controlling the same.

To achieve the objects, according to one aspect of the present invention, there is provided an implantable medical device control system that includes an implantable medical device implanted into a body to stimulate a specific area in the body; a management terminal configured to control driving of the implantable medical device by communicating with the implantable medical device through a wireless communication scheme; and a management server connected to the management terminal to communicate with the management terminal, and configured to assign priority to each parameter included in patient condition information, store and manage the priority, and provide stored information, wherein the management terminal controls the implantable medical device to adjust stimulation applied to the specific area in the body by the implantable medical device to satisfy a reference value preset for all parameters based on the assigned priority.

According to another aspect of the present invention, there is provided a method of controlling an implantable medical device control system, which includes (a) stimulating, by an implantable medical device, a specific area in a body by using power transmitted from an outside of the body in a wireless power transmission scheme; (b) assigning, by a management server, priority to each parameter included in patient condition information, and storing and managing the priority; and (c) controlling, by a management terminal, the implantable medical device to adjust the stimulation applied to the specific area in the body by the implantable medical device based on the assigned priority to satisfy a reference value preset for all parameters.

According to still another aspect of the present invention, there is provided an implantable medical device control system which includes an implantable medical device implanted into a body to stimulate a specific area in the body; a management terminal configured to control driving of the implantable medical device by communicating with the implantable medical device through a wireless communication scheme; and a management server that is connected to the management terminal to communicate with the management terminal, analyzes condition information of a patient corresponding to each parameter for treating a disease of the patient, and provides analyzed information to the management terminal, wherein the management server analyzes all parameters included in the patient condition information, and changes a scheme of controlling the stimulation applied to the specific area in the body based on an analysis result.

According to still another aspect of the present invention, there is provided a method of controlling an implantable medical device control system, which includes (a) stimulating, by an implantable medical device, a specific ea in a body by using power transmitted from an outside of the body in a wireless power transmission scheme; (b) analyzing, by a management server, condition information of a patient corresponding to each parameter for treating a disease of the patient; and (c) controlling, by a management terminal, the implantable medical device to adjust the stimulation applied to the specific area in the body by the implantable medical device based on an analysis result of the management server, wherein the management server analyzes all parameters included in the patient condition information, and changes a scheme of controlling the stimulation applied to the specific area in the body based on an analysis result.

According to still another aspect of the present invention, there is provided an implantable medical device control system which includes an implantable medical device implanted into a body to stimulate a specific area in the body; a management terminal configured to control driving of the implantable medical device by communicating with the implantable medical device through a wireless communication scheme; and a management server that is connected to the management terminal to communicate with the management terminal, analyzes condition information of a patient corresponding to each parameter for treating a disease of the patient, and provides analyzed information to the management terminal, wherein the management server analyzes all parameters included in the patient condition information in association with information on other patients having a same disease, and changes a scheme of controlling the stimulation applied to the specific area in the body based on an analysis result.

According to still another aspect of the present invention, there is provided a method of controlling an implantable medical device control system, which includes (a) stimulating, by an implantable medical device, a specific area in a body by using power transmitted from an outside of the body in a wireless power transmission scheme; (b) analyzing, by a management server, condition information of a patient corresponding to each parameter for treating a disease of the patient in association with information on other patients having a same disease; and (c) controlling, by a management terminal, the implantable medical device to adjust the stimulation applied to the specific area in the body by the implemented medical device based on an analysis result of the management server, wherein the management server analyzes all parameters included in the patient condition information and the information on the other patients, and changes a scheme of controlling the stimulation applied to the specific area in the body based on an analysis result.

As described above, according to the implantable medical device control system and a method of controlling the same of the present invention, by assigning priority to each parameter included in the patient state information, and adjusting stimulation applied to the brain and nerves according to the assigned priority, all parameters may be allowed to satisfy the preset reference value, so that it is possible to control to keep the patient in a stable state.

Thus, according to the present invention, it is possible to alleviate pain or symptoms caused by a disease and maximize the treatment effect.

In addition, according to the present invention, by adjusting stimulation in real time according to the patient condition information, it is possible to increase the patient's satisfaction by increasing the time to maintain the stable state of the patient.

In addition, according to the present invention, by changing the priority of each parameter according to the degree of progression of the disease, change in symptoms, request of the patient, etc., it is possible to alleviate symptoms caused by the disease, improve the treatment effect, and keep the patient in a stable state.

In addition, according to the present invention, it is possible to perform a basic test on the patient condition by using vital sign information including blood pressure, body temperature, and heart rate in the patient condition information, and adjust stimulation according to the test result.

In addition, according to the present invention, it is possible to adjust the stimulation applied to a specific part of the body in real time by analyzing the patient condition information, disease information, and treatment information and selecting an optimal stimulation control scheme.

In addition, according to the present invention, it is possible to alleviate the symptoms caused by the disease, improve the treatment effect, and keep the patient in a stable state by adjusting the stimulation in real time based on the patient condition information.

In addition, according to the present invention, it is possible to improve patient satisfaction by adjusting the stimulation in real time based on the patient condition information and increasing the time to maintain the stabilization state of the EEG.

In addition, according to the present invention, by adjusting the stimulation applied to a specific part of the body in connection with the drug dose information, the dose of the drug can be reduced to prevent overshoot due to an overdose of the drug.

In addition, according to the present invention, by controlling stimulation in connection with drug dose information, even if the dose of the drug is reduced, the time to maintain the patient in a stable state can be increased, thereby improving patient satisfaction.

DETAILED DESCRIPTION OF THE INVENTION

Hereinafter, an implantable medical device control system and a method of controlling the same according to a preferred embodiment of the present invention will be described in detail with reference to the accompanying drawings.

Embodiment 1

The present embodiment will be described using a deep brain stimulation device among implantable medical devices, but the present invention is not limited thereto.

That is, it should be noted that the present invention may be applied to an artificial organ such as a pacemaker or the like which is implanted into the body and used to alleviate or treat symptoms of various diseases by stimulating a specific area in the body, or various implantable medical device control systems such as cochlear implants, gastric stimulators, spinal cord stimulators, cardiac defibrillators, pacemakers, insulin pumps, foot drop implants, and the like.

In addition, the present embodiment is described in which power is supplied to a deep brain stimulation device by wirelessly transmitting power in an ultrasonic wireless charging scheme, but the present invention may be modified to supply power in an electromagnetic wave scheme or a radio frequency scheme as well as the ultrasonic wireless charging scheme.

Figure 1:
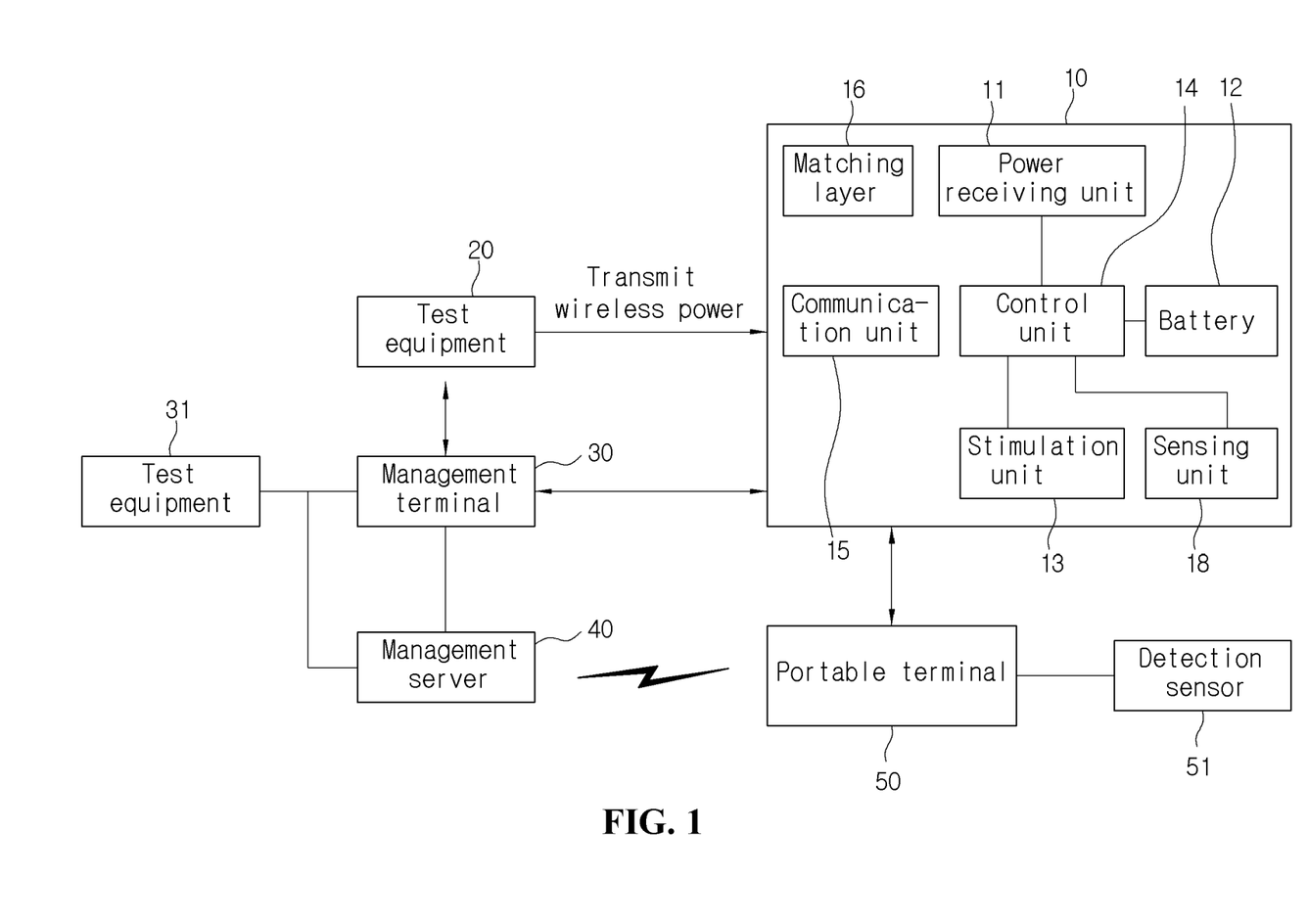
FIG. 1 is a block diagram illustrating a deep brain stimulation device control system according to a first embodiment of the present invention.

FIG. 1 is a block diagram illustrating a deep brain stimulation device control system according to a first embodiment of the present invention.

A deep brain stimulation device control system according to a preferable embodiment of the present invention includes a deep brain stimulation device 10 implanted inside a scalp to stimulate a brain and a nerve, a power transmitter 20 that transmits power from an outside of the body to the deep brain stimulation device 10 in a wireless power transmission scheme using ultrasonic waves, a management terminal 30 that controls the driving of the deep brain stimulation device 10, a management server 40 that is connected the management terminal 30 to communicate with the management terminal 30, stores and manages patient condition information and provides the stored information, and a patient terminal 50 that receives drug information prescribed for a patient through communication with the management terminal 30, and transmits drug dose information and detection information obtained by detecting patient condition to the deep brain stimulation device 10 and the management server 40.

The power transmitter 20 may be provided as an ultrasonic transducer that receives commercial power, converts electrical energy into an ultrasonic signal having a preset frequency, and transmits the converted ultrasonic signal to the deep brain stimulation device 10.

To this end, the power transmitter 20 may include a driving control unit that converts electrical energy into an ultrasonic signal to generate an ultrasonic signal, and controls to transmit the generated ultrasonic signal.

The power transmitter 20 may be provided with a matching layer for matching in acoustic impedance with a power receiving unit 11 of the deep brain stimulation device 10 to be described below.

Through communication with deep brain stimulation device 10, the management terminal 30 receives operation state information of the deep brain stimulation device 10 and information detected by the deep brain stimulation device 10, transmits control commands for operating the deep brain stimulation device 10, and changes or updates a program of the deep brain stimulation device 10.

To this end, the management terminal 30 may include a communication unit (not shown) to enable communication with the management server 40 and wireless communication with the deep brain stimulation device 10.

Such a management terminal 30 may be provided as a doctor terminal through which a doctor checks various information about a prescribed drug or a patient condition in a hospital, prescribes a drug for a patient, and controls the stimulation by the deep brain stimulation device 10.

In addition, the management terminal 30 and the management server 40 are connected to various test equipment 31 to communicate with various test equipment 31 for checking the patient condition such as blood pressure, body temperature, electromyography, electrocardiogram, and electroencephalogram of the patient, and receive test results of each test equipment 31 in real time.

Accordingly, the management terminal 30 may receive the analysis information analyzed by the management server 40, and change, modify, and update a driving program that drives the deep brain stimulation device 10 according to the received analysis information.

In addition, the management terminal 30 may control the driving of the power transmitter 20 in the process of transmitting power in a wireless power transmission scheme.

The management server 40 is communicatively connected to the management terminal 30, each examination equipment 31, and the patient terminal 50 through a local area network or a mobile communication network.

Thus, the management server 40 may control to classify each parameter included in the patient condition information received from the management terminal 30, each examination equipment 31 and the patient terminal 50 into a plurality of groups, assign priority to each classified group or parameter, satisfy all parameters to a preset reference value according to the assigned priority, and maintain the patient condition in a stable state.

For example, Table 1 is a table of parameters related to Parkinson's disease patients.

TABLE 1

| Group | Parameter | Measurement/ detection scheme |
|---|---|---|
| Drug information group | Prescribed medication information, Medication information, Food, health food intake information | Management terminal Patient terminal Patient terminal |
| Biometric information group | Blood pressure, body temperature, | Inspection equipment, Detection sensor |

TABLE 1-continued

| Group | Parameter | Measurement/detection scheme |
|---|---|---|
| | heart rate, etc. | |
| Symptom information group | Symptoms such as pain and tremor | Management terminal, Patient terminal |
| EEG information group | EEG, ECG, EMG, etc. | Test equipment, Detection sensor |
| Walking information group | Walking, turn, Gait freeze information | Test equipment, patient terminal |
| Environment Information Group | Information on changes in the surrounding environment | Test equipment, patient terminal |
| Autonomic Information Group | Sleep time, sleep state | Test equipment, Detection sensor |
| Exercise information group | Exercise time during daily life, Non-exercise time information | Test equipment, patient terminal |
| Other Disease Information Group | Pain from other diseases, Symptom information | Management terminal, patient terminal |

The patient condition information may include not only parameters related to Parkinson's disease, but also various parameters such as information on food consumed by a patient, information on exercise or sleep of a patient, and exercise information related to changes in the surrounding environment.

For example, as shown in Table 1, the management server 40 may classify various parameters included in the patient condition information into a plurality of groups such as a drug information group including information on drugs prescribed for a patient, drug dose information, and information on food or health food consumed by a patient, a biometric information group obtained by detecting a patient's vital signs such as blood pressure, body temperature, and heart rate, a symptom information group obtained by detecting a patient's pain, tremors, or symptoms, EEG information group including EEG obtained by measuring patient's EEG, ECG, EMG, and the like, a gait information group obtained by detecting a gait state, including a patient's gait, turn, and gait freeze information, environmental information group obtained by detecting a movement state according to changes in the surrounding environment, autonomic nervous information group obtained by detecting information on an autonomic nervous system such as sleep time, sleep state, and the like, an exercise information group including information on exercise time during daily life and non-exercise time due to illness, and the other disease information group including other disease information including underlying diseases of a patient such as blood pressure, diabetes, and the like, and other irregular diseases such as colds or headache, and the like.

As an example, the gait information group may include gait information obtained by detecting a gait state including a gait cycle and a stride length of a patient in his daily life, turn information obtained by detecting a turning state when walking, and gait freeze information obtained by detecting a gait freeze state when a specific situation including a change in a width of a road or an alley during walking, and the like occurs.

In addition, the management server 40 may assign a priority to each classified group, analyze and digitize the test or detection information for each parameter, and provide analysis information obtained by analyzing each of digitized information according to the priority assigned to maintain the patient in a stable state to the management terminal 30 and the patient terminal 50.

For example, the management server 40 may store and manage information on drugs administered to a patient, dose information, relative drug price information for each drug, prescription information including timing, period and dose of drugs prescribed for a patient, information on interaction between a drug prescribed for a patient and other drugs other than the corresponding drug, and information on interaction between prescribed drugs and food or health functional food, and may provide the stored information to the management terminal 30 and the patient terminal 50.

The drug information may include the name of each drug prescribed for the patient, the time and period of administration of each drug, the daily dose and the dosage per dose. The drug dose information may be information that the patient actually takes a drug, and the user may check whether the corresponding drug is taken by touching the screen of the patient terminal 50 for each information included in the drug information.

In addition, the management server 40 may update each drug and related information in real time through communication with a drug information management server (not shown) managed by a government agency such as Ministry of Food and Drug Safety.

Accordingly, the management server 40 may manage a dose of a drug, that is, a dopamine formulation, such as a levodopa dose, prescribed for a patient to treat Parkinson's disease.

In addition, the management server 40 may guide a method of taking each drug or prevent prescriptions based on information on interaction between drugs prescribed for treat other diseases of a patient, such as underlying diseases such as diabetes or high blood pressure, or unusual diseases such as cold or abdominal pain.

In addition, the management server 40 may divide and guide the recommended food or health functional food and the prohibited food or the health functional food based on the information on the interaction between the prescribed drug and the food or the health functional food.

Accordingly, a doctor may check the change of each parameter included in the patient condition information, for example, a change in the degree of a disease or whether other diseases have occurred, and the management terminal 30 may change the priorities assigned through communication with the management server 40 according to the operation of the doctor.

In addition, the management terminal 30 may change the priority of each parameter according to the priority requested by the patient, such as relief of pain or symptoms. Meanwhile, in the present embodiment, the management server 40 assigns a basic priority, controls stimulation applied to the brain and nerves according to the priority assigned by the management terminal 30, and controls to change the priority, but the present invention is not necessarily limited thereto.

That is, the present invention may be modified to change the priority assigned to each parameter by the mobile terminal 50 and to control brain and nerve stimulation according to the assigned priority.

In addition, the present invention may be modified such that the deep brain stimulation device 50 itself adjusts brain and nerve stimulation according to the priority assigned by the management terminal 30.

However, in order to prevent the risk of an accident that may occur when the patient directly controls the driving of the deep brain stimulation device 10 by using the patient terminal 50, preferably, the present invention is configured to change and transmit the priority to the deep brain stimulation device 10 only when a patient requests a priority change using the patient terminal 50 and it is approved through a doctor's review process through the management server 40.

The patient terminal 50 transmits detection information for some of the parameters included in the patient's state information to the management server 40, and according to the analysis information received from the management server 40, controls the driving of the deep brain stimulation device 10.

That is, the patient terminal 50 may receive information on a drug prescribed for the patient from the management server 40, receive information on taking the drug from the user (hereinafter, referred to as 'patient') including the patient or guardian, and transmit the information to the deep brain stimulation device 10.

In addition, the patient terminal 50 may receive information on the drug taken by the patient to treat diseases other than Parkinson's disease and food or health functional food information, and transmit the information to the management server 40 and the deep brain stimulation device 10.

To this end, a dedicated application for receiving the patient condition information and controlling the driving of the deep brain stimulation device 10 may be installed in the patient terminal 50 which is provided with various terminals having a wireless communication function, such as a smart phone, a tablet PC, a laptop computer, and the like, which can access to a mobile communication network or a local area network.

In addition, a communication module (not shown) may be provided in the patient terminal 50 to enable communication with the deep brain stimulation device 10 using a short-range wireless communication technology such as Bluetooth.

In addition, the patient terminal 50 may be communicatively connected to a smart device (not shown) having a detecting function such as a smart watch having a function of directly detecting the patient's blood pressure, body temperature, and heart rate, a smart band for detecting the EEG of a patient, etc.

In addition, the patient terminal 50 may be provided with a GPS module for generating movement information of the patient and a detection sensor 51 such as a 3-axis gyro sensor.

Next, the configuration of the deep brain stimulation device will be described in detail with reference to FIGS. 1 and 2.

Figure 2:
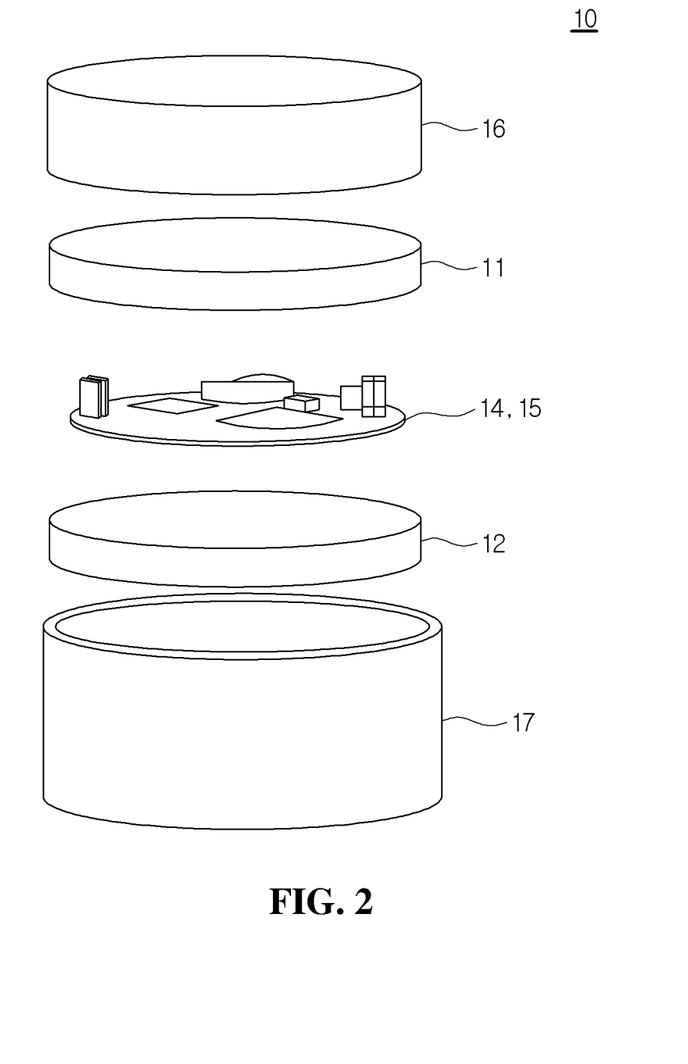
FIG. 2 is an exploded view of the deep brain stimulation device shown in FIG. 1.

FIG. 2 is an exploded view of the deep brain stimulation device shown in FIG. 1.

As shown in FIGS. 1 and 2, the deep brain stimulation device 10 includes a power receiving unit 11 for receiving power transmitted from the power transmitter 20, a battery 12 charged with the power received through the power receiving unit 11, and a stimulation unit 13 for stimulating a brain and a nerve by using the power supplied from the battery 12.

In addition, the deep brain stimulation device 10 may further include a control unit 14 that controls driving of each device provided in the deep brain stimulation device 10, and a communication unit 15 that communicates with the management terminal 30 and the patient terminal 50 in a wireless communication scheme 15.

The power receiving unit 11 may be provided as an ultrasonic transducer that receives power by converting the ultrasonic signal transmitted from the power transmitter 20 into electrical energy.

To this end, the power receiving unit 11 may include a plurality of piezoelectric devices that change the pressure by an ultrasonic signal into a voltage of electrical energy.

The piezoelectric device may be manufactured by using zirconate ($PbZrO_3$) which is a ceramic material having piezoelectricity and pyroelectricity, and lead zirconate titanate (PZT) which is a solid solution of titanate ($PbTiO_3$).

As shown in FIG. 2, the power receiving unit 11, the control unit 14, the communication unit 15, and the battery 12 may be sequentially stacked in the case 80 in a vertical direction, and a matching layer 16 for packaging an upper surface of the case 17 and matching acoustic impedance with the power transmitter 20 may be provided on an upper side of the power receiving unit 11.

That is, the ultrasonic signal transmitted from the power transmitter 20 is transmitted to the power receiving unit 11 through a medium layer such as skin or blood of the human body.

The transmission efficiency of power wirelessly transmitted between the power transmitter 20 and the power receiving unit 11 may be changed according to the characteristics of the medium layer, that is, the material of the medium layer, the geometry, the transmission medium, the attenuation, and the distance between the power transmitter 20 and the power receiving unit 11.

Accordingly, the present invention may minimize the return loss of power transmitted to the power receiving unit 11 by using the material and geometry of the matching layer 16 provided in the power transmitter 20 and the power receiving unit 11, respectively, thereby improving the power transmission efficiency.

The battery 12 may be provided as a rechargeable secondary battery.

The stimulation unit 13 may include an internal micro control unit (not shown) and a stimulation circuit (not shown) for generating a specific stimulation waveform for stimulating the brain and nerves by using the DC power supplied from the battery 12, and a plurality of electrodes for stimulating the brain and nerves according to the stimulation waveform generated by the stimulation circuit.

In this case, each electrode may be provided with a plurality of channels for transmitting stimulation signals to the brain and nerves.

The internal micro control unit may change the current value, voltage value, and period of the stimulation signal that stimulates the brain and nerves according to the control signal of the control unit 14, and change the position and combination of the electrodes that stimulate the brain and nerves among the plurality of electrodes.

Some or all of the electrodes may have a function of detecting an EEG of a patient changed by drugs taken by the patient and brain and nerve stimulation.

As described above, the detection signal obtained by detecting an EEG through the electrode is transmitted to the control unit 14.

The control unit 14 may be provided as a central control unit that controls driving of each device provided in the deep brain stimulation device 10.

The control unit 14 may control the driving of the stimulation unit 13 to control stimulation applied to the brain and nerves by executing a driving program stored in a memory (not shown).

In the process of stimulating the brain and nerves, the control unit 14 may control to transmit load information obtained by detecting the change in the power load due to various factors such as a skin thickness, a degree of hair growth, a blood flow, and the like to the management terminal 30 through the communication unit 15.

In particular, the control unit 14 may generate a control signal to control stimulation applied to the brain and nerves according to the control signal received from the management terminal 30 or the patient terminal 50 and the EEG detection signal detected through each electrode.

Meanwhile, the deep brain stimulation device 10 may further include a sensing unit 18 capable of detecting the above-described load information, and a detection signal output from the sensing unit 18 may be transmitted to the control unit 14.

In addition to the above-described load information, the sensing unit 18 may include a plurality of sensing sensors for detecting various information such as vital signs such as body temperature, blood pressure, heart rate, and respiration volume of the human body, temperature of the battery 12, and an EEG as well as the above-described load information.

Therefore, the control unit 14 may control the stimulus signal to stimulate the brain and nerves in connection with the drug dose information and the EEG detection signal and the detection information detected by the sensing unit 18.

In addition, the control unit 14 may control to change or update the program for driving the stimulation unit 13 according to the control signal received from the management terminal 30 through the communication unit 15.

Next, a method of controlling the deep brain stimulation device control system according to the first embodiment of the present invention will be described in detail with reference to FIG. 3.

Figure 3:
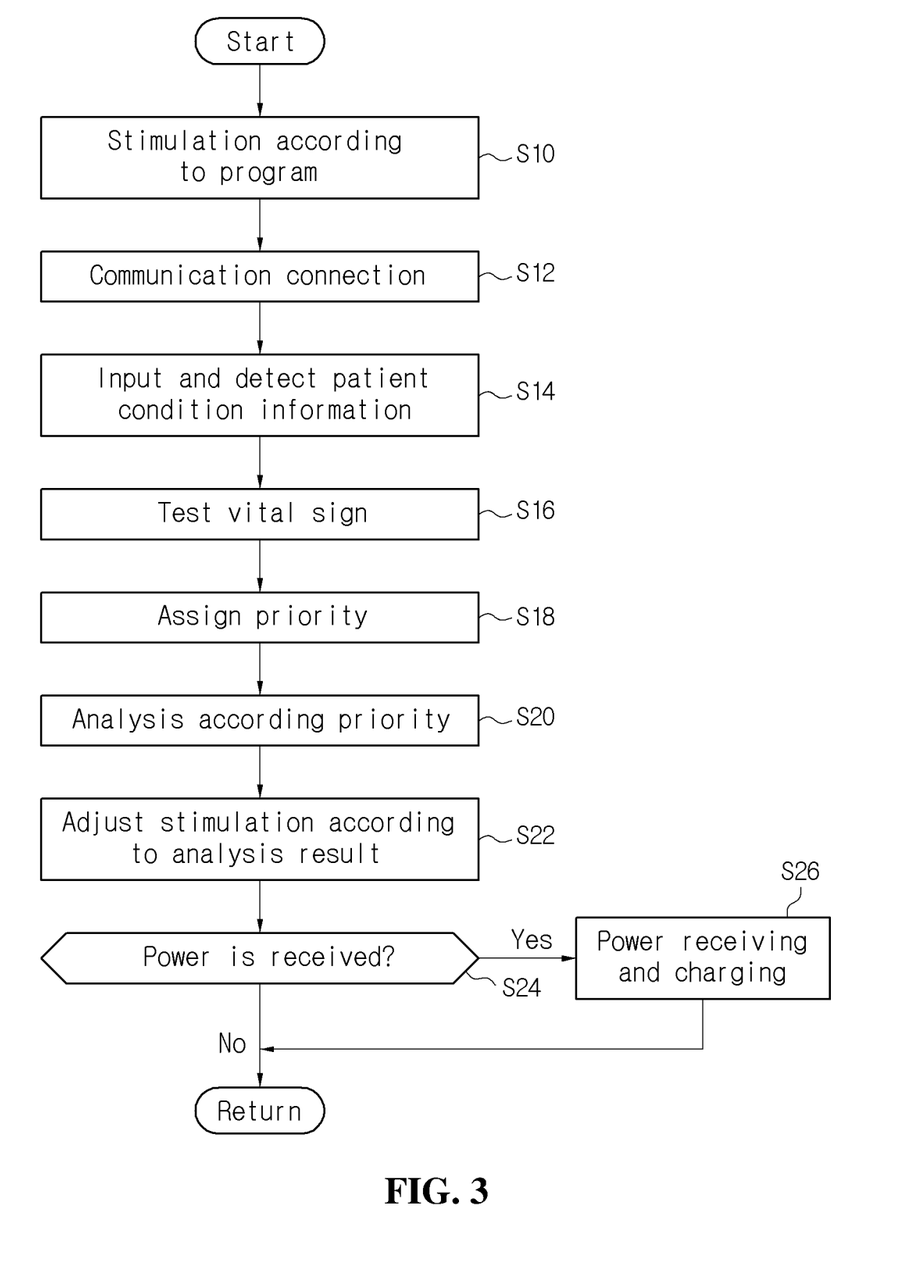
FIG. 3 is a flowchart illustrating step-by-step a method of controlling the deep brain stimulation device control system according to the first embodiment of the present invention.

FIG. 3 is a flowchart illustrating step-by-step a method of controlling the deep brain stimulation device control system according to the first embodiment of the present invention.

In step S10 of FIG. 3, the control unit 14 of the deep brain stimulation device 10 executes a previously stored driving program and controls the driving of the stimulation unit 13 to stimulate the brain and nerves through the plurality of electrodes.

When communication with the management terminal 30 (or the patient terminal 50) is connected through the communication unit 15 of the deep brain stimulation device 10 in step S12, the management terminal 30 assigns priority to all parameters by using the information from the management server 40.

In step S14, the test equipment 31 transmits information about the patient condition such as blood pressure, body temperature, heart rate, electromyography, electrocardiogram, and electroencephalogram (EEG) of the patient to the management terminal 30.

In this case, the detection sensor 51 of the patient terminal 50 and the smart device communicatively connected to the patient terminal 50 may also detect vital sign information in the patient condition information and transmit the vital sign information to the patient terminal 50. The patient terminal 50 may transmit the received detection information and the drug dose information input from the patient to the management server 40, the management terminal 30, and the deep brain stimulation device 10.

Then, in step S16, the management terminal 30 performs a basic test on the patient condition by using the vital sign information including the blood pressure, body temperature, and heart rate in the received patient condition information.

As a result of testing such vital sign information, when the patient is in a normal state, the management terminal 30 assigns priority to all parameters through communication with the management server 40 in step S18. In step S20, the management terminal 30 analyzes and digitizes the detection information and input information of each parameter, and transmits each of digitized information to the deep brain stimulation device 10 to keep the patient in a stable state.

Then, in step S22, the control unit 14 of the deep brain stimulation device 10 receives the analysis result from the management terminal 30, and according to the received analysis result, controls the driving of the stimulation unit 13 to adjust the intensity and period of stimulation applied to the brain and nerves.

As described above, the present invention may assign priority to each parameter included in the patient state information, and adjust stimulation applied to the brain and nerves according to the assigned priority, thereby allowing all parameters to satisfy the preset reference value, so that it is possible to control to keep the patient in a stable state.

Meanwhile, in the process of controlling brain and nerve stimulation according to the patient condition information, in step S24, the control unit 14 checks whether power is received from the power transmitter 20 by using an ultrasonic wireless power transmission technology.

When, as a test result in step S24, power is received, the power receiving unit 11 of the deep brain stimulation device 10 receives the power and charges the battery 12 in step S26.

Then, the control unit 14 returns to step S10 or step S12 to supply the power charged in the battery 12 to each device, and controls to repeat the subsequent steps.

While repeatedly performing such processes, the management terminal 30 may change the priority according to the degree of progression of the disease, change of symptoms, request of the patient, etc., and adjust stimulation applied to the brain and nerves according to the changed priority.

Accordingly, the present invention changes the priority of each parameter according to the degree of progression of the disease, the change of symptoms, and the request of the patient, thereby alleviating the symptoms caused by the disease, improving the treatment effect, and maintaining the patient in a stable state.

Embodiment 2

A deep brain stimulation device control system according to the second embodiment of the present invention has the same configuration as that of the deep brain stimulation device control system described in the first embodiment.

However, in the deep brain stimulation device control system according to the second embodiment of the present invention, the management server 40 is communicatively connected to the management terminal 30, analyzes the patient condition information corresponding to various parameters for treating the disease of the patient, and provides analysis information to the management terminal 30.

The management server 40 may simulate a treatment process after changing the priority based on the patient condition information, and may approve whether to change the priority according to the simulation result.

Meanwhile, the management server 40 may analyze the treatment information and disease progress information as a whole after diagnosis of the patient disease, change the scheme of controlling the stimulation applied to the nerves according to the analysis result, and perform a simulation according to the changed scheme, thereby predicting the treatment effect.

To this end, the management server 40 may provide an optimal stimulation control scheme by using a machine learning scheme for disease information and treatment information of a patient.

Next, a method of controlling a system for controlling a deep brain stimulation device according to a second embodiment of the present invention will be described in detail with reference to FIG. 4.

Figure 4:
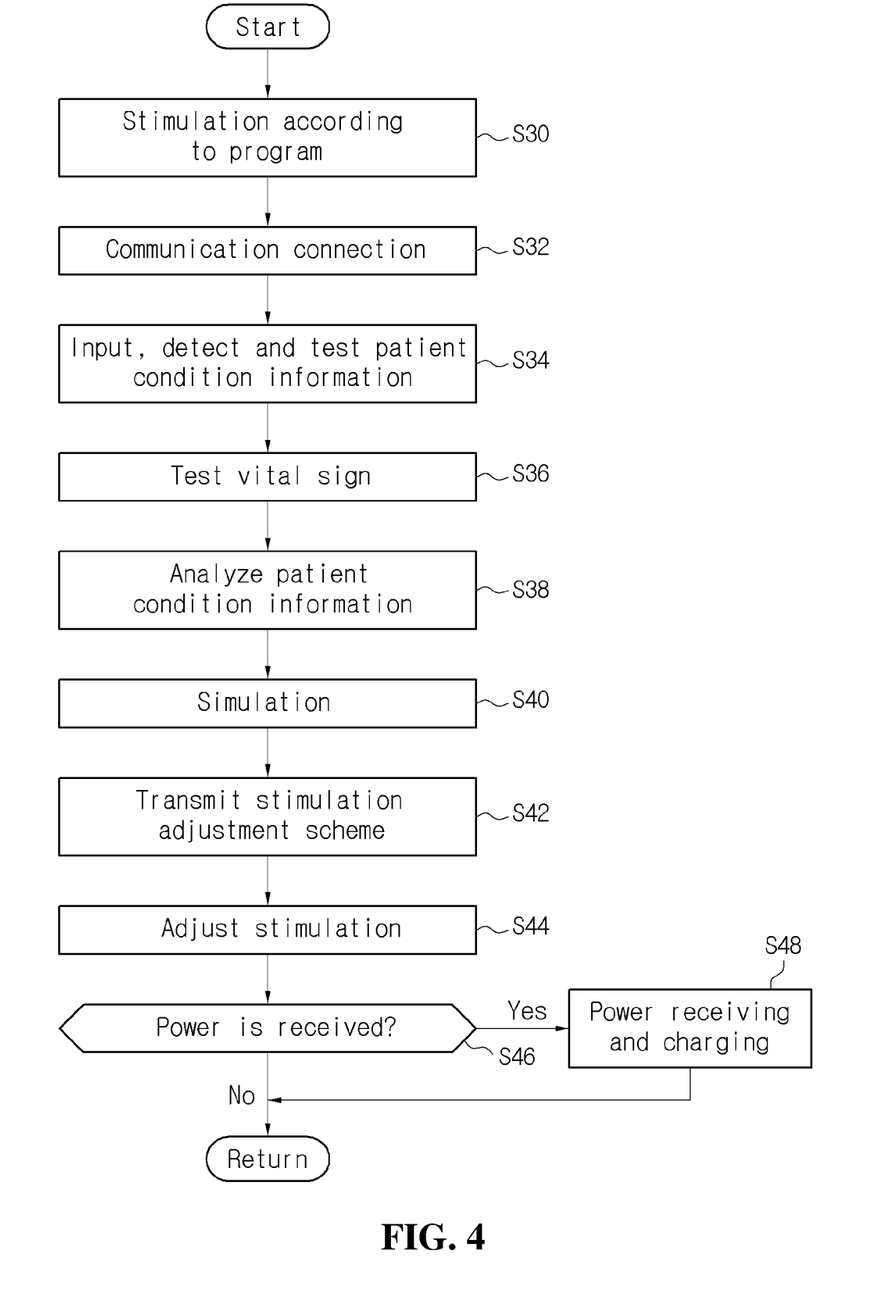
FIG. 4 is a flowchart illustrating step by step a method of controlling a system for controlling a deep brain stimulation device according to a second embodiment of the present invention.

FIG. 4 is a flowchart illustrating step by step a method of controlling a system for controlling a deep brain stimulation device according to a second embodiment of the present invention.

In step S30 of FIG. 4, the control unit 14 of the deep brain stimulation device 10 executes a previously stored driving program and controls the driving of the stimulation unit 13 to stimulate the brain and nerves through a plurality of electrodes.

When communication with the management terminal 30 (or the patient terminal 50) is connected through the communication unit 15 of the deep brain stimulation device 10 in step S32, the management terminal 30 assigns priority to all parameters by using the information from the management server 40.

In step S34, the test equipment 31 transmits information about the patient condition such as blood pressure, body temperature, heart rate, electromyography, electrocardiogram, and electroencephalogram (EEG) of the patient to the management terminal 30.

In this case, the detection sensor 51 of the patient terminal 50 and the smart device communicatively connected to the patient terminal 50 may also detect vital sign information of the patient and transmit the vital sign information to the patient terminal 50. The patient terminal 50 may transmit the received detection information and the drug dose information input from the patient to the management server 40, the management terminal 30, and the deep brain stimulation device 10.

Then, in step S36, the management terminal 30 performs a basic test on the patient condition by using the vital sign information including the blood pressure, body temperature, and heart rate in the received patient condition information.

As a result of testing such vital sign information, in step S38, when the patient is in a normal state, the management terminal 30 transmits the patient condition information to the management server 40, and the management server 40 analyzes the patient condition information in connection with the received patient condition information and the previously stored patient disease information and treatment information.

In step S40, the management server 40 changes the scheme of adjusting the stimulation applied to the nerve according to the analysis result, performs a simulation according to the changed scheme, thereby predicting the treatment effect to select the optimal stimulation adjustment scheme.

In step S42, the stimulation adjustment scheme selected through the above-described process is transmitted to the deep brain stimulation device 10 through the management terminal 30.

Then, in step S44, the control unit 14 of the deep brain stimulation device 10 controls the driving of the stimulation unit 13 to adjust the intensity and period of stimulation applied to the brain and nerves according to the stimulation adjustment scheme received form the management terminal 30.

As described above, the present invention selects the optimal stimulation adjustment scheme by analyzing the patient condition information, disease information, and treatment information, and adjusts stimulation applied to the brain and nerves, thereby allowing all parameters to satisfy the preset reference value, so that it is possible to control to keep the patient in a stable state.

Meanwhile, in step S46, in the process of controlling brain and nerve stimulation according to the patient condition information, the control unit 14 checks whether power is received from the power transmitter 20 by using an ultrasonic wireless power transmission technology.

When, as a test result in step S46, power is received, the power receiving unit 11 of the deep brain stimulation device 10 receives the power and charges the battery 12 in step S48.

Then, the control unit 14 returns to step S30 or step S32 to supply the power charged in the battery 12 to each device, and controls to repeat the subsequent steps.

While repeatedly performing such processes, the management terminal 30 continuously transmits the patient condition information to the management server 40, and the management server 40 analyzes the received patient condition information, disease information, and treatment information to select the optimal stimulation adjustment scheme, so that it is possible to control to adjust the stimulation applied to the brain and nerves.

Accordingly, according to the present invention, the stimulation applied to the brain and nerves may be adjusted in real time based on the patient condition information, so that the symptoms caused by the disease may be alleviated, the treatment effect may be improved, and the patient may be maintained in a stable state.

Embodiment 3

A deep brain stimulation device control system according to the third embodiment of the present invention has the same configuration as that of the deep brain stimulation device control system described in the second embodiment.

However, in the deep brain stimulation device control system according to the third embodiment of the present invention, the management server 40 may be operated in connection with information of another patient having the same disease as the corresponding patient as well as the information of the corresponding patient, thereby providing an optimal stimulation adjustment scheme.

As described above, the present invention may further improve the treatment effect by adjusting the stimulation applied to the brain and nerves in connection with the patient's own information and the information of another patient with the same disease, and may perform treatment with a scheme verified through other patients, so that it is possible to increase the safety for treatment.

Next, a method of controlling a system for controlling a deep brain stimulation device according to the third embodiment of the present invention will be described in detail with reference to FIG. 5.

Figure 5:
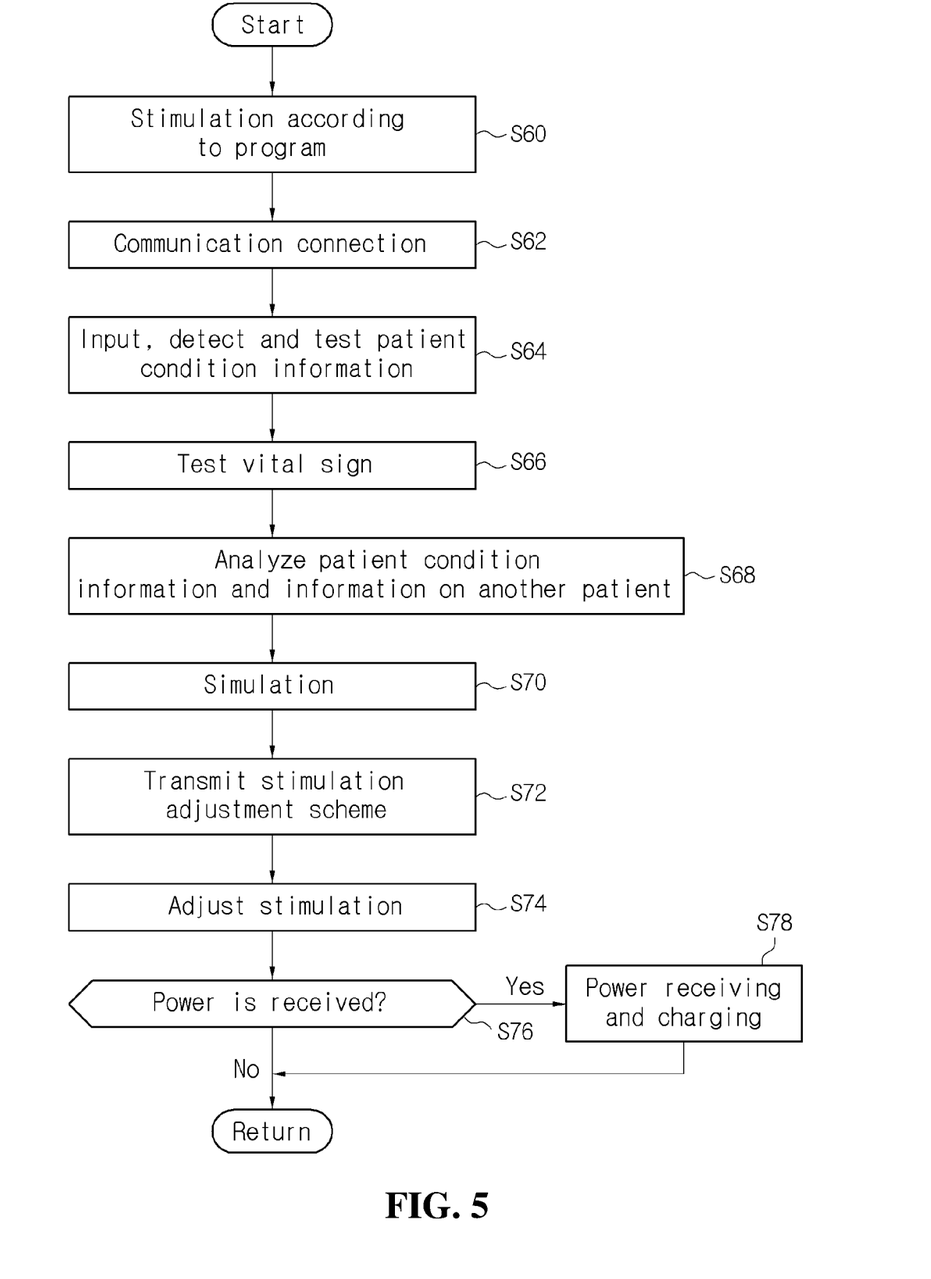
FIG. 5 is a flowchart illustrating step by step a method of controlling a system for controlling a deep brain stimulation device according to the third embodiment of the present invention.

FIG. 5 is a flowchart illustrating step by step a method of controlling a system for controlling a deep brain stimulation device according to the third embodiment of the present invention.

In step S60 of FIG. 5, the control unit 14 of the deep brain stimulation device 10 executes a previously stored driving program and controls the driving of the stimulation unit 13 to stimulate the brain and nerves through a plurality of electrodes.

When communication with the management terminal 30 (or the patient terminal 50) is connected through the communication unit 15 of the deep brain stimulation device 10 in step S62, the management terminal 30 assigns priority to all parameters by using the information from the management server 40.

In step S64, the test equipment 31 transmits information about the patient condition such as blood pressure, body temperature, heart rate, electromyography, electrocardiogram, and electroencephalogram (EEG) of the patient to the management terminal 30.

In this case, the detection sensor 51 of the patient terminal 50 and the smart device communicatively connected to the patient terminal 50 may also detect vital sign information of the patient and transmit the vital sign information to the patient terminal 50. The patient terminal 50 may transmit the received detection information and the drug dose information input from the patient to the management server 40, the management terminal 30, and the deep brain stimulation device 10.

Then, in step S66, the management terminal 30 performs a basic test on the patient condition by using the vital sign information including the blood pressure, body temperature, and heart rate in the received patient condition information.

As a result of testing such vital sign information, in step S68, when the patient is in a normal state, the management terminal 30 transmits the patient condition information to the management server 40, and the management server 40 analyzes the patient condition information in connection with the received patient condition information, the previously stored patient disease information and treatment information, and the information of another patient with the same disease.

In step S70, the management server 40 changes the scheme of adjusting the stimulation applied to the nerve according to the analysis result, performs a simulation according to the changed scheme, thereby predicting the treatment effect to select the optimal stimulation adjustment scheme.

In step S72, the stimulation adjustment scheme selected through the above-described process is transmitted to the deep brain stimulation device 10 through the management terminal 30.

Then, in step S74, the control unit 14 of the deep brain stimulation device 10 controls the driving of the stimulation unit 13 to adjust the intensity and period of stimulation applied to the brain and nerves according to the stimulation adjustment scheme received form the management terminal 30.

As described above, the present invention selects the optimal stimulation adjustment scheme by analyzing the patient condition information, disease information, and treatment information, and adjusts stimulation applied to the brain and nerves, thereby allowing all parameters to satisfy the preset reference value, so that it is possible to control to keep the patient in a stable state.

Meanwhile, in step S76, in the process of controlling brain and nerve stimulation in connection with the condition information of the corresponding patient and the information of another patient, the control unit 14 checks whether power is received from the power transmitter 20 by using an ultrasonic wireless power transmission technology.

When, as a test result in step S76, power is received, the power receiving unit 11 of the deep brain stimulation device 10 receives the power and charges the battery 12 in step S48.

Then, the control unit 14 returns to step S60 or step S62 to supply the power charged in the battery 12 to each device, and controls to repeat the subsequent steps.

While repeatedly performing such processes, the management terminal 30 continuously transmits the patient condition information to the management server 40, and the management server 40 analyzes the received patient condition information, disease information, and treatment information in connection with the information of another patient to select the optimal stimulation adjustment scheme, so that it is possible to control to adjust the stimulation applied to the brain and nerves.

Accordingly, according to the present invention, the stimulation applied to the brain and nerves may be adjusted in real time based on the patient condition information, so that the symptoms caused by the disease may be alleviated, the treatment effect may be improved, and the patient may be maintained in a stable state.

In addition, the present invention may further improve the treatment effect by adjusting the stimulation applied to the brain and nerves in connection with the patient's own information and the information of another patient with the same disease, and may perform treatment with a scheme verified through other patients, so that it is possible to increase the safety for treatment.

As described above, although the invention made by the present inventor has been described in detail with reference to the embodiments, the invention is not limited to the above embodiments, and may be variously modified without departing from the scope.

In the above embodiments, the configuration of a deep brain stimulation device among implantable medical devices has been described, but the present invention may be applied to an artificial organ such as a pacemaker or the like which is implanted into the body and used to alleviate or treat symptoms of various diseases by stimulating a specific area in the body, or various implantable medical device such as cochlear implants, gastric stimulators, spinal cord stimulators, cardiac defibrillators, pacemakers, insulin pumps, foot drop implants, and the like.

Further, in the above embodiments, it has been described that the stimulation unit and the sensing unit are provided at the same time. However, the present invention may be applicable to a medical device which is provided only with a sensing unit, such as a nerve stimulator stimulating nerves and a brain machine interface (BMI), to detect only load information or biometric information without stimulation.

In addition, in the above embodiment, it has been described that power is supplied to the deep brain stimulation device by transmitting power wirelessly in an ultrasonic wireless charging scheme, but the present invention may be modified to supply not only an ultrasonic wireless charging scheme, but also an electromagnetic wave scheme or a radio frequency scheme.

The present invention is applied to techniques of an implantable medical device control system and a method of controlling the same that transmit power to a medical device implanted in the body in a wireless power transmission scheme using ultrasonic waves.

What is claimed is:

1. An implantable medical device control system comprising:
   an implantable medical device configured to be implanted into a body to stimulate a specific area in the body;
   a management terminal configured to control driving of the implantable medical device by communicating with the implantable medical device through a wireless communication scheme; and
   a management server configured to communicate with the management terminal, and the management server further configured to assign a priority to each parameter of a plurality of parameters included in patient condition information, store the patient condition information, manage the priority, and provide the stored patient condition information, wherein the management server divides the plurality of parameters included in the patient condition information into a plurality of groups, assigns the priority to each group of the plurality of groups, analyzes and digitizes test or detection information for each parameter of the plurality of parameters, and provides analysis information of the digitized information to the management terminal according to the assigned priority, wherein the management terminal, by using the analysis information provided from the management server, satisfies a reference value preset for all the plurality of parameters based on the assigned priority so that a patient is maintained in a stable state, wherein the management terminal performs a basic test on a condition of the patient by using vital sign information comprising a blood pressure, a body temperature, and a heart rate in the received patient condition information, and adjust the stimulation applied to the specific area in the body when the condition of the patient is normal as a test result, and wherein the priority of the plurality of parameters is changed based on a disease progression degree, a symptom change, and a request of the patient.

2. The implantable medical device control system of claim 1, further comprising:

a power transmitter for transmitting power from an outside of the body to the implantable medical device in a wireless power transmission scheme using an ultrasonic wave; and a patient terminal for receiving drug information prescribed for the patient through a communication with the management terminal, detecting dose information of corresponding drug and the patient condition information, and transmitting the detected information to the implantable medical device and the management server, wherein the management terminal controls the driving of the implantable medical device based on the detected information and test information received from the patient terminal and a test equipment that communicates with the management terminal.

3. A method of controlling an implantable medical device control system, the method comprising:

(a) stimulating, by an implantable medical device, a specific area in a body by using power transmitted from an outside of the body in a wireless power transmission scheme;

(b) assigning, by a management server, a priority to each parameter of a plurality of parameters included in_patient condition information, and storing and managing the priority;

(c) controlling, by a management terminal, the implantable medical device to adjust the stimulation applied to the specific area in the body by the implantable medical device based on the assigned priority to satisfy a reference value preset for all the plurality of parameters;

(d) performing, by the management terminal, a basic test on a condition of a patient by using vital sign information comprising a blood pressure, a body temperature, and a heart rate in the patient condition information; and (e) changing, by the management terminal, the assigned priority through a communication with the management server in response to a disease progression degree, a symptom change, and a request of the patient, wherein, in the step (b), the management server divides the plurality of parameters included in the patient condition information into a plurality of groups, assigns the priority to each group, analyzes and digitizes test or detection information for each parameter of the plurality of parameters, and provides analysis information of the digitized information to the management terminal according to the assigned priority, and wherein, in the step (c), the management terminal controls, by using the analysis information provided from the management server, the implantable medical device to adjust stimulation applied to the specific area in the body based on the assigned priority.

* * * * *